(12) United States Patent
Jacobs et al.

(10) Patent No.: US 10,369,036 B2
(45) Date of Patent: *Aug. 6, 2019

(54) VERTICALLY ORIENTED BAND FOR STOMACH

(71) Applicant: Advanced Bariatric Technology, LLC, Coral Gables, FL (US)

(72) Inventors: Moises Jacobs, Miami, FL (US); Moises Jacobs, III, Miami, FL (US)

(73) Assignee: ADVANCED BARIATRIC TECHNOLOGY, LLC, Coral Gables, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/605,812

(22) Filed: May 25, 2017

(65) Prior Publication Data

US 2017/0258619 A1 Sep. 14, 2017

Related U.S. Application Data

(63) Continuation of application No. 14/531,300, filed on Nov. 3, 2014, now Pat. No. 9,737,429, which is a
(Continued)

(51) Int. Cl.
*A61F 5/00* (2006.01)
*A61B 17/122* (2006.01)

(52) U.S. Cl.
CPC .......... *A61F 5/0086* (2013.01); *A61B 17/122* (2013.01)

(58) Field of Classification Search
CPC .. A61F 5/0083; A61F 5/0086; A61B 17/0643; A61B 17/0682; A61B 17/083;
(Continued)

(56) References Cited

U.S. PATENT DOCUMENTS

| 600,887 A | 3/1898 | Pettit |
| 3,254,651 A | 6/1966 | Collito |

(Continued)

FOREIGN PATENT DOCUMENTS

| AU | 201399422 | 2/2017 |
| AU | 2017200911 | 12/2018 |

(Continued)

OTHER PUBLICATIONS

Office Action for U.S. Appl. No. 11/797,537 dated Jul. 16, 2009 (10 pages).

(Continued)

*Primary Examiner* — Carrie R Dorna
(74) *Attorney, Agent, or Firm* — Foley & Lardner LLP (57) ABSTRACT

An adjustable band or clamp or non-adjustable clamp is placed about the greater curvature of the stomach in a vertical orientation. The band or clamp completely compartmentalizes the stomach between a small vertical pouch and the fundus and body of the stomach. The fundus and body of the stomach are excluded from nutrients and are separated from a long narrow channel where the food travels. A small passage at the level of the antrum allows gastric juices to empty from the fundus and body of the stomach. The clamp may be applied during open surgery in laproscopic surgery or using a single port technique, or through any natural orifice in NOTES (Natural Orifice Transluminal Endoscopic surgery) or using a hybrid surgical technique.

19 Claims, 5 Drawing Sheets

Related U.S. Application Data continuation of application No. 11/984,452, filed on Nov. 19, 2007, now Pat. No. 8,920,305, which is a continuation-in-part of application No. 11/797,537, filed on May 4, 2007, now abandoned.

(60) Provisional application No. 60/881,138, filed on Jan. 19, 2007.

(58) Field of Classification Search
CPC . A61B 17/128; A61B 17/1285; A61M 39/284
See application file for complete search history.

(56) References Cited

U.S. PATENT DOCUMENTS

| | | | |
|---|---|---|---|
| 3,316,914 A | 5/1967 | Collito | |
| 3,417,752 A | 12/1968 | Butler | |
| 3,766,925 A | 10/1973 | Rubricius | |
| 4,060,089 A | 11/1977 | Noiles | |
| 4,274,415 A | 6/1981 | Kanamoto et al. | |
| 4,346,869 A * | 8/1982 | MacNeill | A61M 39/284 |
| | | | 251/10 |
| 4,390,019 A | 6/1983 | LeVeen et al. | |
| 4,414,721 A | 11/1983 | Hufnagel | |
| 4,428,374 A | 1/1984 | Auburn | |
| 4,458,681 A | 7/1984 | Hopkins | |
| 4,548,202 A | 10/1985 | Duncan | |
| 4,558,699 A | 12/1985 | Bashour | |
| 4,610,250 A | 9/1986 | Green | |
| 4,803,985 A | 2/1989 | Hill | |
| 4,950,284 A | 8/1990 | Green et al. | |
| 4,976,721 A | 12/1990 | Blasnik et al. | |
| 5,062,846 A | 11/1991 | Oh et al. | |
| 5,074,868 A | 12/1991 | Kuzmak | |
| 5,127,915 A | 7/1992 | Mattson | |
| 5,156,609 A | 10/1992 | Nakao et al. | |
| 5,163,945 A | 11/1992 | Ortiz et al. | |
| 5,226,429 A | 7/1993 | Kuzmak | |
| 5,234,454 A | 8/1993 | Bangs | |
| 5,236,437 A | 8/1993 | Wilk et al. | |
| 5,250,058 A | 10/1993 | Miller et al. | |
| 5,327,914 A | 7/1994 | Shlain | |
| 5,345,949 A | 9/1994 | Shlain | |
| 5,423,831 A | 3/1995 | Nates | |
| 5,428,871 A | 7/1995 | Iosif | |
| 5,456,714 A | 10/1995 | Owen | |
| 5,464,416 A | 11/1995 | Steckel | |
| 5,549,621 A | 8/1996 | Bessler et al. | |
| 5,575,802 A | 11/1996 | McQuilkin et al. | |
| 5,766,189 A | 6/1998 | Matsuno | |
| 5,901,993 A | 5/1999 | Lowery et al. | |
| 6,036,704 A | 3/2000 | Yoon | |
| 6,179,850 B1 | 1/2001 | Goradia | |
| 6,273,903 B1 | 8/2001 | Wilk | |
| 6,464,710 B1 | 10/2002 | Foster | |
| 6,503,258 B1 | 1/2003 | Filho | |
| 6,537,289 B1 | 3/2003 | Kayan et al. | |
| 6,572,629 B2 | 6/2003 | Kalloo et al. | |
| 6,694,982 B2 | 2/2004 | Latour | |
| 6,716,226 B2 | 4/2004 | Sixto, Jr. et al. | |
| 6,814,742 B2 | 11/2004 | Kimura et al. | |
| 6,869,438 B2 | 3/2005 | Chao | |
| 6,926,724 B1 | 8/2005 | Chu | |
| 6,981,978 B2 | 1/2006 | Gannoe | |
| 7,022,126 B2 | 4/2006 | De Canniere | |
| 7,105,000 B2 | 9/2006 | McBrayer | |
| 7,135,032 B2 | 11/2006 | Akerfeldt | |
| 7,214,233 B2 | 5/2007 | Gannoe et al. | |
| 7,223,229 B2 | 5/2007 | Inman et al. | |
| 7,232,445 B2 | 6/2007 | Kortenbach et al. | |
| 7,261,725 B2 | 8/2007 | Binmoeller | |
| 7,288,100 B2 | 10/2007 | Molina Trigueros | |
| 7,320,701 B2 | 1/2008 | Haut et al. | |
| 7,338,503 B2 | 3/2008 | Rosenberg et al. | |
| 7,416,528 B2 | 8/2008 | Crawford et al. | |
| 7,645,285 B2 | 1/2010 | Cosgrove et al. | |
| 7,691,053 B2 | 4/2010 | Viola | |
| 7,758,493 B2 | 7/2010 | Gingras | |
| 7,871,416 B2 | 1/2011 | Phillips | |
| 7,892,244 B2 | 2/2011 | Monassevitch et al. | |
| 8,287,559 B2 | 10/2012 | Barker et al. | |
| 8,382,775 B1 | 2/2013 | Bender et al. | |
| 8,529,585 B2 | 9/2013 | Jacobs et al. | |
| 8,920,305 B2 | 12/2014 | Jacobs et al. | |
| 9,808,257 B2 | 11/2017 | Armenteros et al. | |
| 9,814,614 B2 | 11/2017 | Jacobs et al. | |
| 2002/0022851 A1 | 2/2002 | Kalloo et al. | |
| 2002/0082625 A1 | 6/2002 | Huxel et al. | |
| 2002/0138086 A1 | 9/2002 | Sixto et al. | |
| 2004/0082963 A1 | 4/2004 | Gannoe et al. | |
| 2004/0097989 A1 | 5/2004 | Molina Trigueros | |
| 2004/0116945 A1 | 6/2004 | Sharkawy et al. | |
| 2004/0147942 A1 | 7/2004 | Chao | |
| 2005/0075652 A1 | 4/2005 | Byrum et al. | |
| 2005/0119674 A1 | 6/2005 | Gingras | |
| 2005/0125014 A1 | 6/2005 | Duluco et al. | |
| 2005/0149069 A1 | 7/2005 | Bertolero et al. | |
| 2005/0197714 A1 | 9/2005 | Sayet | |
| 2005/0216042 A1 | 9/2005 | Gertner | |
| 2005/0250980 A1 | 11/2005 | Swanstrom et al. | |
| 2005/0251158 A1 | 11/2005 | Saadat et al. | |
| 2005/0277959 A1 | 12/2005 | Cosgrove et al. | |
| 2006/0011699 A1 | 1/2006 | Olson et al. | |
| 2006/0074440 A1 | 4/2006 | Garner | |
| 2006/0157067 A1 | 7/2006 | Saadat et al. | |
| 2006/0200179 A1 | 9/2006 | Barker et al. | |
| 2006/0217757 A1 | 9/2006 | Horndeski | |
| 2006/0252983 A1 | 11/2006 | Lembo et al. | |
| 2006/0264981 A1 | 11/2006 | Viola | |
| 2006/0264982 A1 | 11/2006 | Viola et al. | |
| 2006/0264987 A1 | 11/2006 | Sgro | |
| 2007/0021761 A1 | 1/2007 | Phillips | |
| 2007/0032807 A1 | 2/2007 | Ortiz et al. | |
| 2007/0088190 A1 | 4/2007 | Appel | |
| 2007/0149989 A1 | 6/2007 | Santilli et al. | |
| 2007/0167962 A1 | 7/2007 | Gannoe et al. | |
| 2007/0185373 A1 | 8/2007 | Tsonton | |
| 2007/0213747 A1 | 9/2007 | Monassevitch et al. | |
| 2007/0265644 A1 | 11/2007 | Ichihara et al. | |
| 2008/0033457 A1 | 2/2008 | Francischelli et al. | |
| 2008/0039879 A1 | 2/2008 | Chin et al. | |
| 2008/0082114 A1 | 4/2008 | McKenna et al. | |
| 2008/0092910 A1 | 4/2008 | Brooks | |
| 2008/0177292 A1 | 7/2008 | Jacobs et al. | |
| 2008/0208324 A1 | 8/2008 | Glithero et al. | |
| 2008/0275480 A1 | 11/2008 | Jacobs et al. | |
| 2008/0287976 A1 | 11/2008 | Weaner et al. | |
| 2008/0319435 A1 | 12/2008 | Rioux et al. | |
| 2009/0137870 A1 | 5/2009 | Bakos et al. | |
| 2009/0138009 A1 | 5/2009 | Viswanathan et al. | |
| 2009/0198266 A1 | 8/2009 | Cesare | |
| 2010/0030017 A1 | 2/2010 | Baker et al. | |
| 2010/0174295 A1 | 7/2010 | Kassab et al. | |
| 2011/0046641 A1 | 2/2011 | Kassab et al. | |
| 2011/0092993 A1 | 4/2011 | Jacobs | |
| 2011/0092998 A1 | 4/2011 | Hirszowicz et al. | |
| 2011/0098732 A1 | 4/2011 | Jacobs | |
| 2011/0190791 A1 | 8/2011 | Jacobs et al. | |
| 2011/0245593 A1 | 10/2011 | Kassab et al. | |
| 2012/0095484 A1 | 4/2012 | Dominguez | |
| 2012/0123463 A1 | 5/2012 | Jacobs | |
| 2014/0012293 A1 | 1/2014 | Bertolero et al. | |
| 2014/0046345 A1 | 2/2014 | Armenteros et al. | |
| 2014/0074131 A1 | 3/2014 | Armenteros et al. | |
| 2014/0200598 A1 | 7/2014 | Kassab et al. | |
| 2015/0051624 A1 | 2/2015 | Jacobs et al. | |
| 2017/0360447 A1 | 12/2017 | Armenteros et al. | |
| 2018/0008447 A1 | 1/2018 | Jacobs et al. | |
| 2019/0021892 A1 | 1/2019 | French | |

FOREIGN PATENT DOCUMENTS

| | | |
|---|---|---|
| CN | 105007838 A | 10/2015 |
| CO | 30415 | 12/2016 |

(56) References Cited

FOREIGN PATENT DOCUMENTS

| | | |
|---|---|---|
| DE | 19751733 A1 | 12/1998 |
| DE | 29822558 U1 | 2/1999 |
| EP | 0201344 A2 | 11/1986 |
| EP | 0220643 A2 | 5/1987 |
| EP | 1397998 A1 | 3/2004 |
| EP | 1547529 A1 | 6/2005 |
| EP | 1600108 A2 | 11/2005 |
| EP | 1749506 A1 | 2/2007 |
| EP | 1806101 A1 | 7/2007 |
| EP | 1882451 A2 | 1/2008 |
| EP | 2 528 512 B1 | 12/2012 |
| EP | 3185784 A1 | 7/2017 |
| EP | 3398538 | 11/2018 |
| JP | 9289989 A | 11/1997 |
| JP | 2002085414 A | 3/2002 |
| JP | 2007044517 A | 2/2007 |
| JP | 2007097664 A | 4/2007 |
| JP | 2007159794 A | 6/2007 |
| NZ | 704680 A | 5/2017 |
| RU | 2262896 C2 | 6/2005 |
| RU | 2386455 C2 | 4/2010 |
| RU | 2626875 C2 | 8/2017 |
| TH | 158414 | 12/2016 |
| TH | 174586 | 3/2018 |
| WO | WO 1980001752 A1 | 9/1980 |
| WO | WO-9833437 A1 | 8/1998 |
| WO | WO-1998033437 A1 | 8/1998 |
| WO | WO-1999/11179 A1 | 3/1999 |
| WO | WO-9911179 A1 | 3/1999 |
| WO | WO-0078234 A1 | 12/2000 |
| WO | WO-2000076432 A1 | 12/2000 |
| WO | WO-2000078234 A1 | 12/2000 |
| WO | WO-2002064041 A1 | 8/2002 |
| WO | WO-2004017839 A1 | 3/2004 |
| WO | WO-2005/046453 A2 | 5/2005 |
| WO | WO-2006033385 A1 | 3/2006 |
| WO | WO-2006044640 A1 | 4/2006 |
| WO | WO-2007013995 A2 | 2/2007 |
| WO | WO-2008081436 A2 | 7/2008 |
| WO | WO-2008091537 A2 | 7/2008 |
| WO | WO-2008101048 A2 | 8/2008 |
| WO | WO-2011094700 A1 | 8/2011 |
| WO | WO-2016033221 A1 | 3/2016 |
| WO | WO-2018009669 A1 | 1/2018 |
| WO | WO-2019/023279 A1 | 1/2019 |

OTHER PUBLICATIONS

Office Action for U.S. Appl. No. 11/797,537 dated Jan. 7, 2010 (9 pages).
Office Action cited in U.S. Appl. No. 11/984,452, dated Aug. 5, 2009 (13 pgs).
Final Office Action cited in U.S. Appl. No. 11/984,452, dated Mar. 26, 2010 (11 pgs).
Examiner's Interview Summary cited in U.S. Appl. No. 11/984,452, dated Jun. 11, 2010 (5 pgs).
Office Action cited in U.S. Appl. No. 11/984,452, dated Aug. 6, 2012 (10 pgs).
Final Office Action cited in U.S. Appl. No. 11/984,452, dated Jan. 31, 2013 (12 pgs).
Office Action cited in U.S. Appl. No. 11/984,452, dated May 20, 2013 (14 pgs).
Copending U.S. Appl. No. 13/963,998, filed Aug. 9, 2013; Inventors: Jesus R. Armenteros et al.
Copending U.S. Appl. No. 14/021,720, filed Sep. 9, 2013; Inventors: Jesus R. Armenteros et al.
PCT International Search Report cited in Patent Application No. PCT/US2008/000644, dated Jul. 7, 2008 (1 pg).
International Preliminary Report on Patentability cited in PCT/US2008/000644, dated Nov. 17, 2009 (4 pgs).
Written Opinion cited in PCT/US2008/000644, dated Jul. 7, 2008 (3 pgs).
PCT International Search Report and Written Opinion cited in Patent Application No. PCT/US2011/023205, dated Apr. 5, 2011 (13 pgs).
International Preliminary Report on Patentability cited in PCT/US2011/023205, dated Jul. 31, 2012 (10 pgs).
Copending International Patent Application No. PCT/US2013/54435 filed Aug. 9, 2013; First Named Inventor: Armenteros, Jesus R.
International Search Report cited in PCT/US2013/54435, dated Jan. 16, 2014 (2 pgs).
Written Opinion cited in PCT/US2013/54435 dated Jan. 16, 2014 (8 pgs).
Helmut Kapczynski, Surgical Instruments 101, An Introduction to Kmedic Certified Instruments, Kmedic, Inc., 1997, Northvale, New Jersey (181 Pages).
An espace English abstract of JP-9289989-A (Nov. 11, 1997).
Patent Abstract of Japan of JP-2002085414-A (Mar. 26, 2002).
Patent Abstract of Japan of JP-2007044517-A (Feb. 22, 2007).
An espace English abstract of JP-2007097664-A (Apr. 19, 2007).
An espace English abstract of JP-2007159794-A (Jun. 28, 2007).
An espace English abstract of DE-19751733 (Dec. 10, 1998).
Communication and Supplementary European Search Report of EP Application No. EP11737828, dated Sep. 23, 2014.
Machine Translation of DE29822558 U1.
Copending U.S. Appl. No. 62/042,117, filed Aug. 26, 2014; first named inventor: Jesus R. Armenteros.
Copending U.S. Appl. No. 14/531,300, filed Nov. 3, 2014; Inventors: Moises Jacobs et al.
Response to Office Action in U.S. Appl. No. 11/984,452 dated Oct. 3, 2013.
Final Office Action cited in U.S. Appl. No. 11/984,452 dated Jan. 30, 2014.
RCE and Response to Final Office Action in U.S. Appl. No. 11/984,452, dated May 30, 2014.
Applicant-Initiated Interview Summary in U.S. Appl. No. 11/984,452, dated May 30, 2014.
Notice of Allowance in U.S. Appl. No. 11/984,452 dated Jun. 30, 2014.
Machine Translation of DE23922558 U1 (Feb. 18, 1999).
Office Action for U.S. Appl. No. 14/021,720 dated Oct. 7, 2014 (6 pgs).
Response to Office Action for U.S. Appl. No. 14/021,720 dated Dec. 3, 2014 (8 pgs).
Office Action for U.S. Appl. No. 14/021,720 dated Jan. 2, 2015 (8 pgs).
Response to Office Action for U.S. Appl. No. 14/021,720 dated Apr. 2, 2015 (13 pgs).
Copending U.S. Appl. No. 62/118,455, filed Feb. 19, 2015; first named inventor: Jesus R. Armenteros.
Office Action for U.S. Appl. No. 14/531,300 dated Dec. 29, 2014 (14 pages).
International Preliminary Report on Patentability cited in PCT/US2013/054435, dated Jun. 9, 2015 (9 pgs).
Response to Office Action for U.S. Appl. No. 14/531,300 dated Jun. 26, 2015 (13 pages).
Office Action for U.S. Appl. No. 14/531,300 dated Oct. 19, 2015 (7 pages).
Office Action for U.S. Appl. No. 14/021,720 dated Jun. 12, 2015 (9 pgs).
Response to Office Action for U.S. Appl. No. 14/021,720 dated Oct. 12, 2015 (10 pgs).
Examiner initiated Interview Summary, Advisory Action, and AFCP 2.0 Decision in U.S. Appl. No. 14/021,720, dated Oct. 29, 2015 (7 pgs).
Copending U.S. Appl. No. 14/836,621, filed Aug. 26, 2015; First-Named Inventor: Jesus R. Armenteros.
Copending International Patent Application No. PCT/US2015/47005 filed Aug. 26, 2015; First Named Inventor: Moises Jacobs.
Jacobs, Moises, et al., Presentation, "A Novel Procedure for Bariatric and Metabolic Surgery, a weight loss clamp" Apr. 2015 (20 pgs).
"A Pathway to Endoscopic Bariatric Therapies" Gastrointestinal Endoscopy Journal, www.giejournal.org, vol. 74, No. 5 (2011), pp. 943-953.

(56) References Cited

OTHER PUBLICATIONS

Search Report of copending Singapore Application No. SG11201500782R, dated Oct. 8, 2015.
Written Opinion of copending Singapore Application No. SG11201500782R, dated Oct. 12, 2015.
Copending International Patent Application No. PCT/US2013/54435 filed Aug. 9, 2013, entitled "Polymer Overmolded Bariatric Clamp and Method of Installing"; First Named Inventor: Armenteros, Jesus R.
Machine Translation of DE23922558 U1.
International Search Report and Written Opinion of PCT/US2015/047005, dated Nov. 27, 2015.
International Search Report dated Nov. 27, 2015 in corresponding PCT Appln. PCT/US2015/047005, 13 pages.
Copending U.S. Appl. No. 62/359,529, filed Jul. 7, 2016; first named inventor: Jesus R. Armenteros.
Final Office Action for U.S. Appl. No. 14/021,720 dated Jul. 14, 2016 (14 pgs).
Office Action, Translation and Search Report in Russian Patent Application No. 2015108054, (May 27, 2016), 6 pgs.
Office Action, Translation and Search Report in Russian Patent Application No. 2015108054, (Oct. 26, 2016), 6 pgs.
Response to Russian Office Action in Application No. 2015108054, (Aug. 30, 2016), 1 pg.
Response to Written Opinion of copending Singapore Application No. SG11201500782R, dated Mar. 31, 2016, 6 pgs.
First Examination Report of New Zealand Patent Application 704680, dated May 20, 2016, 6 pgs.
Response to First Examination Report of New Zealand Patent Application 704680, dated Dec. 19, 2016, 3 pgs.
Supplementary European Search Report in EP Application No. EP13828055.7, dated Aug. 31, 2016, 5 pgs.
Office Action in Columbian Patent Application No. 15053467, (dated Jul. 21, 2016), 7 pgs.
Office Action in Chinese Patent Application No. 2013800523046, (dated Dec. 19, 2016), 9 pgs.
Office Action in Canadian Application No. 2880155, dated Feb. 17, 2016, 5 pgs.
Response to Office Action in Canadian Application No. 2880155, dated Aug. 17, 2016, 4 pgs.
Office Action in Canadian Application No. 2880155, dated Nov. 23, 2016, 4 pgs.
Examiner's Report dated Oct. 21, 2015 in Au Application No. 2013299422, 3 pgs.
Response to Examiner's Report dated Oct. 21, 2015 in AU Application No. 2013299422, (Jul. 8, 2016), 31 pgs.
Communication Pursuant to Article 94(3) EPC from EPO in EP Application No. EP11737828, Jun. 8, 2016, 6 pgs.
Response to Communication Pursuant to Article 94(3) EPC from EPO in EP Application No. EP11737828, dated Dec. 19, 2016, 19 pgs.
Office Action Restriction Requirement for U.S. Appl. No. 13/963,998 dated Jun. 1, 2016 (8 pgs).
Response to Office Action Restriction Requirement for U.S. Appl. No. 13/963,998 dated Jul. 7, 2016 (16 pgs).
Office Action for U.S. Appl. No. 13/963,998 dated Nov. 15, 2016 (13 pgs).
Response to Final Office Action for U.S. Appl. No. 14/021,720 dated Oct. 13, 2016 (9 pgs).
Advisory Action and Interview Summary for U.S. Patent App. No. 14/021,720 dated Oct. 27, 2016 (5 pgs).
Response to Advisory Action for U.S. Appl. No. 14/021,720 dated Nov. 10, 2016 (9 pgs).
Notice of Allowance for U.S. Appl. No. 14/021,720 dated Dec. 27, 2016 (8 pgs).
Response to Office Action for U.S. Appl. No. 14/531,300 dated Mar. 21, 2016 (9 pgs).
Notice of Allowance for U.S. Appl. No. No. 14/531,300 dated Apr. 12, 2016 (7 pgs).
Rule 312 Amendment for U.S. Appl. No. 14/531,300 dated Jun. 8, 2016 (3 pgs).
Notice of Allowance for U.S. Appl. No. 14/531,300 dated Oct. 24, 2016 (7 pgs).
Geoffrey W.J. Vertical Ligated Gastroplasty by Clamp, Cut and Suture: A Series of 504 Cases Dating Back to 1977.0bes Surg. Nov. 1994;4(4):344-348, PMID: 10742799 [PubMed—as supplied by publisher], 5 pgs.
Notice of Acceptance in AU Application No. 2013299422, (dated Nov. 1, 2016), 2 pgs.
Request for Substantive Examination and Claim Amendments in BR Application No. BR 112015 0027253, (dated Jul. 11, 2016), 13 pgs.
Response to Russian Office Action in Application No. 2015108054, (Jan. 26, 2017), 1 pg.
Response Brief filed in Columbian Patent Application No. 15053467, (dated Sep. 22, 2016), 6 pgs.
Shalimov, et al., Intestinal Track Surgery, Kiev, "Dzorovya", 1987, c. 558, 2 pgs.
Further Examination Report of New Zealand Patent Application 704680, dated Jan. 24, 2017, 3 pgs.
Response to Office Action for U.S. Appl. No. 13/963,998 dated Nov. 15, 2016, filed Feb. 10, 2017 (18 pgs).
International Preliminary Report on Patentability of PCT/US2015/047005, dated Mar. 9, 2017.
Notice of Eligibility for Grant of copending Singapore Application No. SG11201500782R, dated Mar. 20, 2017.
Examination Report of copending Singapore Application No. SG11201500782R, dated Mar. 9, 2017, 9 pgs.
Response to Supplementary European Search Report in EP Application No. EP13828055.7, dated Mar. 27, 2017, 14 pgs.
Decision of Grant in Russian Application No. 2015108054, (dated Mar. 15, 2017), 16 pg.
Final Office Action for U.S. Appl. No. 13/963,998 dated Apr. 18, 2017 (16 pgs).
Response to Office Action in Chinese Patent Application No. 2013800523046, filed Apr. 10, 2017, 12 pgs.
Notice of Allowance for U.S. Appl. No. 14/021,720 dated May 16, 2016 (5 pgs).
Response to Office Action dated Nov. 23, 2016 in Canadian Application No. 2880155, dated Apr. 24, 2017.
Response to Further Examination Report of New Zealand Patent Application 704680, dated Jan. 24, 2017, filed Apr. 21, 2017,22 pgs.
Response to Final Office Action for U.S. Appl. No. 13/963,998 dated Apr. 18, 2017, filed Jun. 6, 2017 (14 pgs).
Notice of Acceptance of New Zealand Patent Application 704680, dated May 10, 2017, Published on May 26, 2017 in Journal 1655.
Certificate of Grant of copending Singapore Application No. SG11201500782R, dated Jun. 15, 2017.
freedictionary.com definition of "stretchable", accessed on Aug. 2, 2017, http://www.thefreedictionary.com/stretchable.
U.S. Appl. No. 13/963,998, Non-Final Office Action dated Aug. 21, 2017 (23 pgs).
U.S. Appl. No. 14/836,621, Non-Final Office Action dated Aug. 22, 2017 (16 pgs).
Copending U.S. Appl. No. 15/677,227, filed Aug. 15, 2017; First-Named Inventor: Jesüs R. Armenteros.
Office Action in Canadian Application No. 2880155, dated Aug. 24, 2017, 14 pgs.
Response to Office Action dated Aug. 24, 2017 in Canadian Application No. 2880155, filed Sep. 27, 2017.
Second Office Action in Chinese Patent Application No. 2013800523046, (dated Jul. 27, 2017), 12 pgs.
International Search Report and Written Opinion of PCT/US17/40908, dated Sep. 11, 2017.
Publication of Co-pending Singapore Patent Application No. 10201704073T, Jun. 29, 2017, 1 pg.
Copending U.S. Appl. No. 62/536,364, filed Jul. 24, 2017; first named inventor: C. Kenneth French.
Copending International Patent Application No. PCT/US17/40908 filed Jul. 6, 2017; First Named Inventor: Jesus R. Armenteros.
Singapore Patent Application No. 11201701503Y, Request for Voluntary Amendment filed Aug. 8, 2017.

(56) References Cited

OTHER PUBLICATIONS

Copending U.S. Appl. No. 15/642,919, filed Jul. 6, 2017; First-Named Inventor: Moises Jacobs.
U.S. Appl. No. 13/963,998, Response to Final Office Action with RCE dated Jul. 11, 2017 (12 pgs).
U.S. Appl. No. 14/836,621, Final Office Action dated Mar. 16, 2018 (17 pgs.).
Communication and Partial Supplementary European Search Report of EP Application No. EP15837010.6, dated May 11, 2018, 10 pgs.
Full Examination Report dated Apr. 18, 2018 in AU Application No. 2017200911, 2 pgs.
Examination Report in Dominican Republic Application No. P2017-0051 dated Apr. 19, 2018, 6 pgs.
Search Report dated Apr. 19, 2018 in Singapore Pat. App. No. 11201701503Y, 3 pgs.
Written Opinion dated Apr. 17, 2018 in Singapore Pat. App. No. 11201701503Y, 8 pgs.
U.S. Appl. No. 13/963,998, Final Office Action dated Apr. 18, 2018 (29 pgs).
International Search Report and Written Opinion of PCT/US18/43562, dated Nov. 21, 2018, 17 pgs.
Examination Report in Dominican Republic Application No. P2015-0023 dated May 22, 2018, 4 pgs.
U.S. Appl. No. 13/963,998, Non-Final Office Action dated Aug. 8, 2018 (36 pgs).
U.S. Appl. No. 14/836,621, Non-Final Office Action dated Jul. 6, 2018 (13 pgs).
PCT International Patent Application No. PCT/US2017/040908, International Preliminary Report on Patentability and Notification dated Jan. 17, 2019, 9 pgs.
U.S. Appl. No. 13/963,998, Final Office Action dated Feb. 7, 2019, 36 pgs.
U.S. Appl. No. 14/836,621, Final Office Action dated Jan. 31, 2019, 11 pgs.
U.S. Appl. No. 14/836,621, Advisory Action dated Apr. 10, 2019, 6 pgs.
U.S. Appl. No. 14/836,621, Notice of Allowance, dated Apr. 30, 2019, 13 pgs.
U.S. Appl. No. 13/963,998, Notice of Allowance, dated May 30, 2019, 11 pgs.
U.S. Appl. No. 15/677,227, Non-Final Office Action, dated Jun. 13, 2019, 10 pgs.

* cited by examiner

VERTICALLY ORIENTED BAND FOR STOMACH

CROSS-REFERENCE TO RELATED APPLICATIONS

Pursuant to 35 U.S.C. § 120, this application is a continuation of, and incorporates by reference for all purposes, U.S. patent application Ser. No. 14/531,300, entitled "Vertically Oriented Band for Stomach," filed Nov. 3, 2014, and naming Moises Jacobs and Moises Jacobs III as inventors, which is a continuation of, and incorporates by reference for all purposes, U.S. patent application Ser. No. 11/984,452, entitled "Vertically Oriented Band for Stomach," filed Nov. 19, 2007, and naming Moises Jacobs and Moises Jacobs III as inventors, which is a continuation-in-part of U.S. patent application Ser. No. 11/797,537, entitled "Vertically Oriented Band for Stomach," filed May 4, 2007, and naming Moises Jacobs and Moises Jacobs III as inventors, which claims the benefit of U.S. Provisional Application No. 60/881,138, entitled "Vertically Oriented Band for Stomach," filed Jan. 19, 2007, and naming Moises Jacobs as inventor, all of which are incorporated by reference for all purposes.

BACKGROUND

For patients whose obesity presents an immediate serious health risk, surgical procedures are available to promote weight loss. Two of the most common surgical procedures are gastric bypass and gastric band. During gastric bypass, the stomach is made smaller and food bypasses part of the small intestine. The smaller size stomach causes the patient to eat less and the bypass of the small intestines leads to less calories being absorbed by the body.

In the most common type of gastric bypass surgery, roux-en-y, a small pouch is formed at the top of the stomach using staples. The smaller stomach is connected to the middle portion of the small intestines bypassing the upper portion of the small intestines.

Devices have been developed to form the smaller stomach from the patient's original stomach. One such device is disclosed in U.S. Patent Publication No. 2002/0022851 to Kalloo et al. (Kalloo). Kalloo discloses a loop 80 reducing the volume of the gastric cavity. A feeder line is pulled to reduce the diameter of the loop and collapse the walls of the stomach to define a smaller pouch.

U.S. Patent Publication No. 2006/0157067 to Saadat et al. (Saadat) discloses the use of tissue anchors to form a gastric pouch acting as a restriction to the passage of fluids and food. U.S. Pat. No. 5,345,949 to Shlain (Shlain) discloses a clip placed across the fundus of the stomach to restrict the inlet chamber or proximal pouch. Likewise, U.S. Pat. No. 6,869,438 to Chao (Chao) discloses a gastric partitioning clip creating a stomach pouch from the stomach to restrict the amount of food intake.

It is an object of the invention to provide a device for separating the stomach into two compartments but allowing communication between the compartments.

It is another object of the invention to provide a device for forming a smaller stomach pouch, the size of the pouch being tailored to the patient's individual circumstances.

It is another object of the invention to provide a procedure creating a small stomach pouch to limit intake of food separate from the stomach but allowing gastric juices from the excluded stomach to flow into the pouch.

It is still another object of the invention to provide a system for creating a small pouch from the main stomach that is reversible.

It is still another object of the invention to alter the production of hormones, enzymes and chemicals that affect metabolism, energy levels, hunger, digestion, absorption of nutrients, weight loss, maintenance or gain that may be affected by exclusion of the gastric fundus and body of the stomach.

These and other objects of the invention will become apparent after reading the disclosure of the invention.

SUMMARY

An adjustable band or clamp or non-adjustable clamp is placed about the greater curvature of the stomach in a vertical orientation. The band or clamp completely compartmentalizes the stomach between a small vertical pouch and the fundus and body of the stomach. The fundus and body of the stomach are excluded from nutrients and are separated from a long narrow channel where the food travels. A small passage at the level of the antrum allows gastric juices to empty from the fundus and body of the stomach. The clamp may be applied during open surgery in laproscopic surgery or using a single port technique, or through any natural orifice in NOTES (Natural Orifice Transluminal Endoscopic surgery) or using a hybrid surgical technique.

DETAILED DESCRIPTION OF THE DRAWINGS

Figure 1:
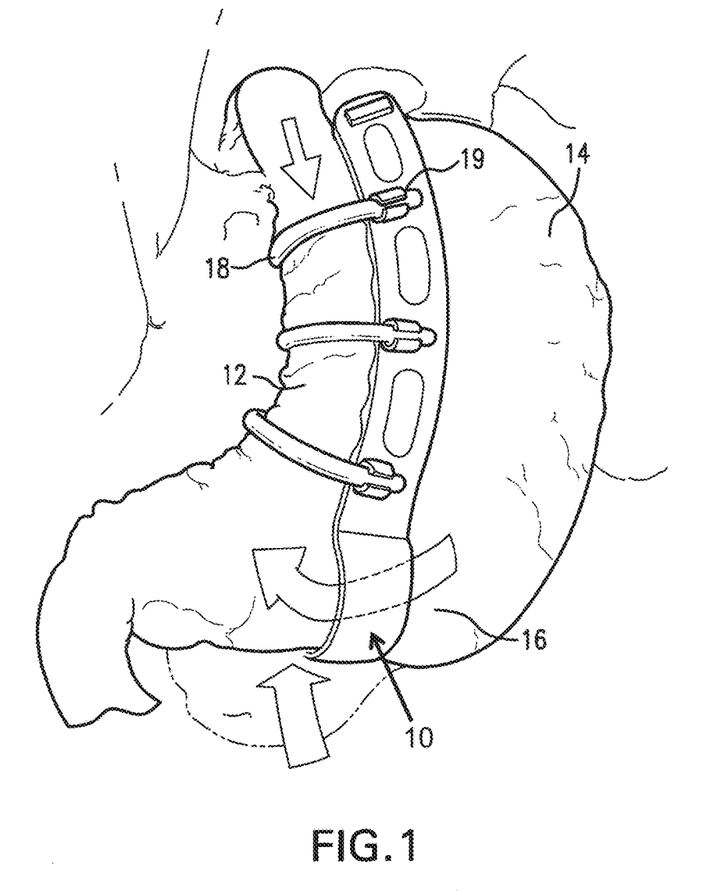
FIG. 1 is a view of the band applied to a stomach.

In FIG. 1, a stomach having the band 10 applied can be seen dividing the stomach into the pouch 12 and fundic and body area 14. Food traveling down the esophagus enters the pouch 12 and exits into the antrum. The band 10 applies pressure against the sides of the stomach to separate the stomach into the two compartments, but does not apply pressure to the stomach walls at the bottom part of the stomach. This creates a passage 16 allowing flow of gastric juices from the fundic and body area 14 into the antrum. Food will not enter the fundic and body of the stomach through this passage, however. At least one horizontal strap 18 may be used to secure the band in place. The straps may be adjustable and may apply pressure sufficient to impact the size and function of the pouch 12.

Figure 2:
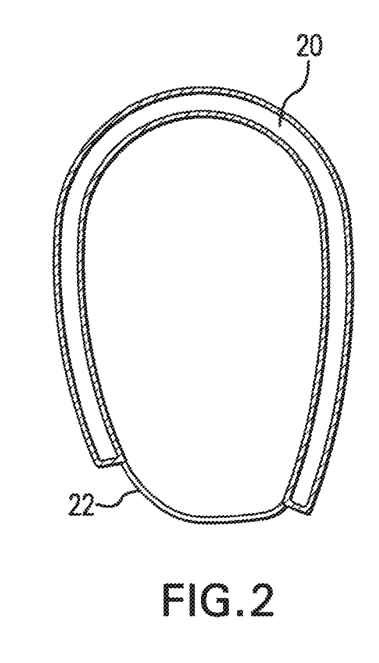
FIG. 2 is a cross-sectional view of an inflatable clamp useable with the invention.

FIG. 2 shows an embodiment of the clamp having an inflatable chamber 20 and a connecting section 22. The clamp is placed about the stomach in a vertical orientation to separate the stomach into the two compartments and inflated. The clamp may have an asymmetrically placed chamber 20, that when inflated applies pressure on the stomach to seal the two compartments from one another except for the passage 16. The connecting section 22, being not inflated, does not apply pressure to the bottom portion of the stomach, allowing for the formation of the passage 16. In addition, the clamp may have an asymmetrically placed inflatable chamber that faces the lesser curvature side of the stomach, that when inflated or deflated only alters the lumen of the vertical compartment through which the nutrients pass and does not play a role in the creation of the two compartments.

Figure 3:
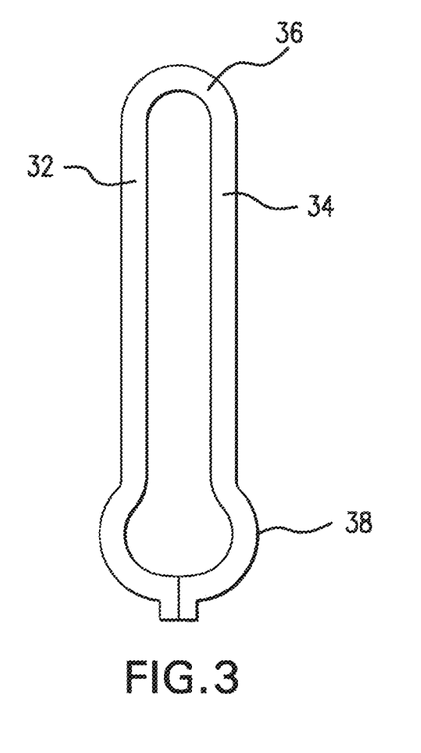
FIG. 3 is a view of a non-adjustable clamp used with the invention.

FIG. 3 shows the rigid clamp embodiment having a U portion formed by two legs 32, 34 connected by a bight portion 36. When the clamp is placed on the stomach, the bight portion 36 fits over the top of the stomach with the legs 32, 34 applying enough pressure to collapse the walls of the stomach against one another to create the two compartments. The legs 32, 34 may or may not extend the full vertical extent of the stomach to allow for the creation of the passage 16. The legs are attached by a connector 38. When applied to the stomach, the legs serve to push the sides of the stomach together to form a complete seal but the connector allows for the formation of a passage between the two compartments. The clamp may be adjustable. The legs of the clamp may be made or adjusted to any length depending on the size of the stomach the legs can be made shorter or longer. The two legs may be connected by a magnetic coupler rather than a solid bight portion but may not be connected at all at the proximal end of the stomach. The apposition of the clamp legs about the stomach must be accomplished without sufficient force to cause ischemia of the gastric walls when the legs are closed.

Besides a clip, the vertical band may be formed as or with an inflatable balloon, as discussed with reference to FIG. 2. The orientation of the balloon is such that, upon inflation, the balloon bulges to the left to decrease the size of the compartment 12. The bottom portion may or may not be inflatable. The balloon may be attached to a tube exiting the body so that the balloon may be adjusted without the need for invasive surgery.

Figure 4:
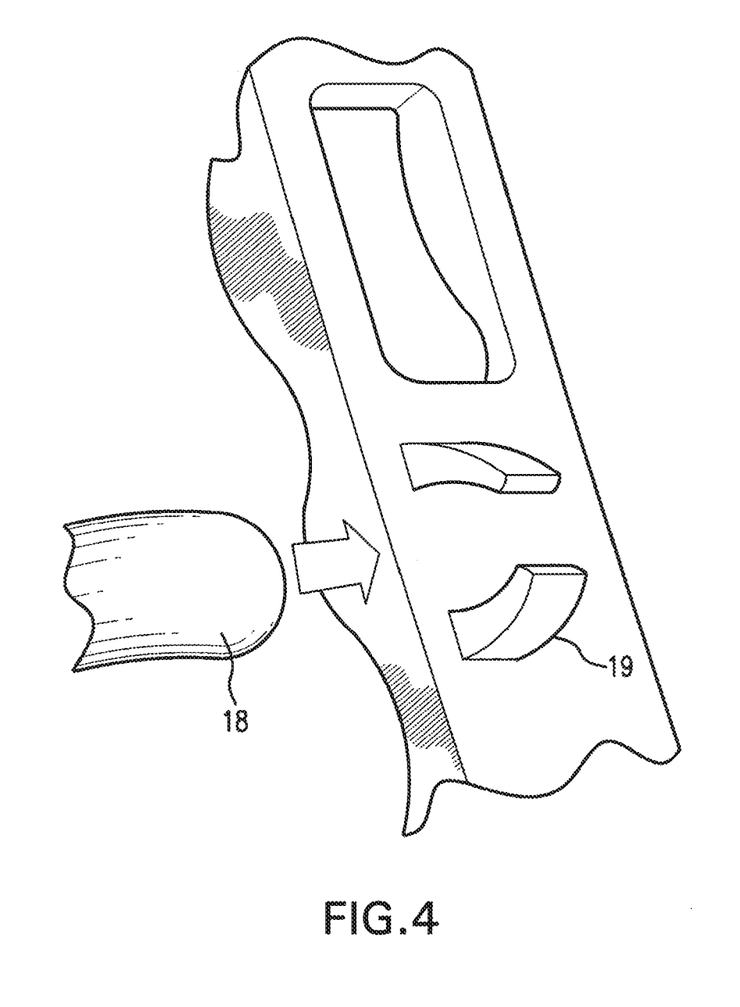
FIG. 4 is a detailed view of the strap attachment to the band.

Straps 18 can be secured to the band in any number of conventional ways. One possible way in which to secure the straps to the band is depicted in FIG. 4. The band engages and is secured by clips 19 which extend outwardly from the band. This arrangement allows the straps to be tightened by being pulled through the clip and, if desired, the straps can be released for the removal of the band. These straps may also have an inflatable chamber and may be adjustable so as to also increase or decrease the lumen of the vertical compartment through which the nutrients pass.

Figure 5:
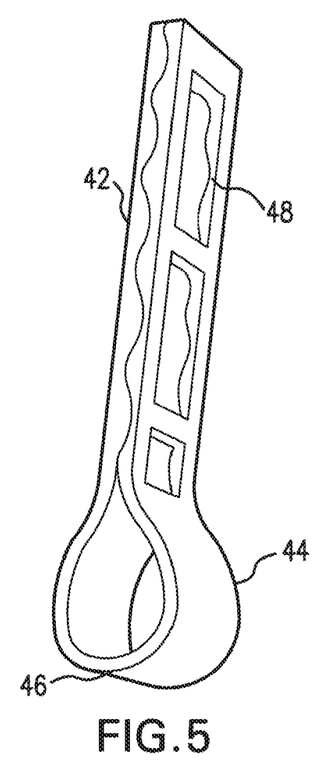
FIG. 5 is a perspective view of a second embodiment of the band.

An alternative construction of the band is seen in FIG. 5. In this embodiment, the band has a first section 42 having two parallel arms and a second section with two space members so that, when applied to a stomach, the passageway 16 is formed. The clamp itself may be curved to allow for better accommodation about the lesser curvature. The arms may be straight, curved or undulating. The surface may be smooth or serrated. The arms of the first section 42 are resiliently biased against one another and are spaced from one another in order that, when applied, the first section maintains the walls of the stomach together to separate the stomach into the first and second compartments. The pressure applied must be enough that the two compartments are formed but not so much that the walls of the stomach are damaged or compromise the blood supply. The section 44 is connected together by a section 46 acting as a hinge. This allows the arms of the first section 42 to be separated from one another in order that the band may be applied. Conversely, it is possible to have the two arms of the first section 42 hinged to one another and the two arcuate portions forming the second section 44 not connected to one another.

Figure 6:
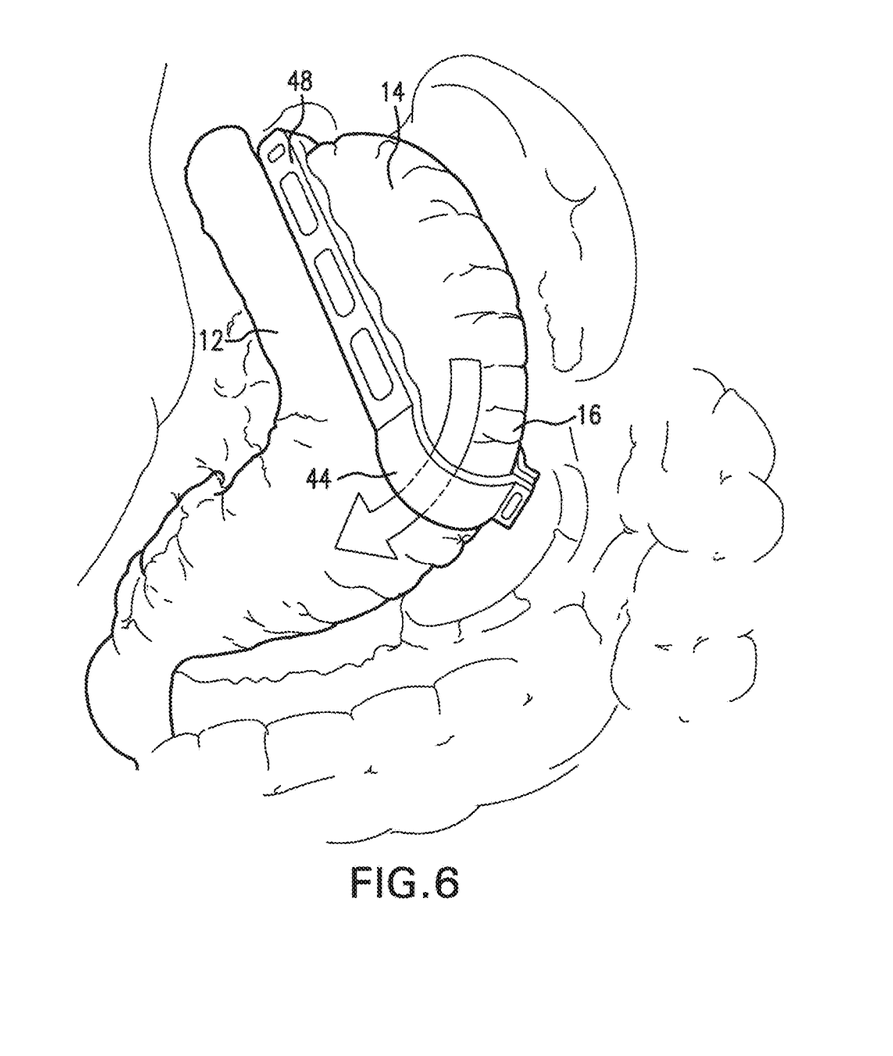
FIG. 6 is a view of the band in FIG. 5 applied to a stomach.

The band of FIG. 5 applied to stomach is seen in FIG. 6. Seen here as the first section 42 extending along the stomach to separate the stomach into two compartments, including pouch 12 and fundic and body area 14, whereas the second section has arcuate arms forming a passage 16. At least one of the arms of the first section is provided with apertures 48. The apertures, which may be large or small, allow part of the stomach wall to enter the aperture to help prevent movement of the band once it has been applied.

There are many ways in which the clamp can be applied including Natural orifice transluminal endoscopic surgery (NOTES) and the combination of NOTES and an assistant trochar placed in to the abdominal cavity. Combinations include any combination of the conventional, laproscopic, NOTES and one port techniques. The NOTES technique includes transgastric, transvaginal, transrectal, transcolonic and combinations of these. Another possibility is the one port technique wherein one port is used for the introduction of several instruments. The one port technique encompasses a one port abdominal (including umbilical), perineal, retroperitoneal approaches and combinations of these.

To facilitate application of the band, a bougie may be utilized in any suitable manner, such as placed transorally, transgastrically or transintestinally. The bougie, having a vacuum suction apparatus, collapses the stomach wall to align and help the placement the clamp. To help with alignment and placement of the clamp, the bougie may have magnets to mate with the magnets or metallic areas when the clamp is provided with such. Also, the band may be made of bioabsorbable material to negate the need to remove it.

While the invention has been described with reference to preferred embodiments, various modifications would be apparent to one of ordinary skill in the art. The invention encompasses such variations and modifications.

What is claimed is:

1. A gastric band configured to be positioned on a stomach to partition the stomach into a first portion and a second portion, and to provide a passage between the first and second portions of the stomach, the gastric band comprising:
   a partitioning section comprising a first end of the gastric band having a first arm with a bent end and a first elongate member extending a majority of a length of the gastric band and a second arm with a bent end and a second elongate member extending a majority of the length of the gastric band and spaced apart a first distance from the first elongate member;
   a passage-forming section comprising a second end of the gastric band, and having a curved member joining together the bent ends of the first and second arm of the partitioning section and spacing the bent ends apart by a second distance greater than the first distance; and
   an inflatable portion comprising at least a portion of at least one of the partitioning section and the passage-forming section.

2. The gastric band of claim 1, wherein the curved member is one-piece from the joining of the bent end of the first arm to the joining of the bent end of the second arm.

3. The gastric band of claim 1, wherein the first and second arms of the partitioning section are in a parallel relation to one another.

4. The gastric band of claim 1, further comprising one or more opening in at least one of the first or second arms of the partitioning section.

5. The gastric band of claim 1, wherein the inflatable portion comprises at least a portion of the partitioning section.

6. The gastric band of claim 1, further comprising a biasing section configured to bias at least the first and second arms of the partitioning section to form the first and second portions of the stomach.

7. The gastric band of claim 6, wherein the biasing section is further configured to bias the first and second passage-forming portions to form the passage between the first and second portions of the stomach.

8. The gastric band of claim 6, wherein the biasing section is disposed towards the distal end of the gastric band.

9. The gastric band of claim 6, wherein the biasing section is disposed towards the proximal end of the gastric band.

10. The gastric band of claim 6, wherein the biasing section comprises at least one of a hinge, bight portion, and magnetic coupler.

11. The gastric band of claim 1, wherein the gastric band further comprises at least one strap coupled to the first and second arms of the partitioning section.

12. A gastric band, comprising:
a first section having first and second arms spaced from one another a first distance when positioned on a stomach and configured to close walls of the stomach together to form a first compartment of the stomach and a second compartment of the stomach, said first section extending a majority of a length of said gastric band;
a second section disposed at an end of the gastric band opposite the first section, the second section having first and second portions, the first portion coupled with the first arm of the first section at a bent end of the first arm and the second portion coupled with the second arm of the first section at a bent end of the second arm, and the first and second portions at least partially spaced from one another a second distance at the bent ends greater than the first distance, the second section configured to form a passage between the first compartment of the stomach and the second compartment of the stomach, wherein the second section is curved along its entire length, positioning the first and second arms opposite the second section and cantilevering from the second section; and
an inflatable portion, wherein the inflatable portion is at least a portion of at least one of the first section and the second section.

13. The gastric band of claim 12, wherein the first compartment of the stomach comprises a food pouch and the second compartment of the stomach comprises a fundic region.

14. The gastric band of claim 12, wherein the passage formed by the second section provides a passage from the second compartment into an antrum of the stomach.

15. The gastric band of claim 12, further comprising a biasing section configured to bias at least the first and second arms of the first section to form the first and second compartments of the stomach.

16. The gastric band of claim 12, wherein the second section serves as a biasing section configured to bias at least the first and second arms of the first section.

17. The gastric band of claim 12, wherein the inflatable portion comprises at least a portion of the first section.

18. A gastric band to partition a stomach into a first portion and a second portion, and to provide a passage between the first and second portions of the stomach, the gastric band comprising:

a partitioning section comprising a distal end of the gastric band;
a passage-forming section comprising a curved proximal end of the gastric band;
wherein the partitioning section comprises:
a first arm extending a majority of a length of the gastric band; and
a second arm extending the majority of the length of the gastric band,
wherein the second arm is spaced apart from the first arm by a first distance to partition the stomach into the first and second portions;
wherein the passage-forming section comprises:
a caudal-most curved portion extending toward the first arm and the second arm of the partitioning section,
a first passage-forming portion,
wherein the first passage-forming portion is at least partially curved,
wherein the first passage-forming portion is adjacent to the first arm of the partitioning section, and
wherein the first passage-forming portion extends substantially in a cranial direction towards the partitioning section;
a second passage-forming portion,
wherein the second passage-forming portion is at least partially curved,
wherein the second passage-forming portion is adjacent to the second arm of the partitioning section,
wherein the second passage-forming portion is adjacent to the first passage-forming portion, and
wherein the second passage-forming portion extends substantially in the cranial direction towards the partitioning section;
wherein the first passage-forming portion and the second passage forming portion are both united to the caudal-most curved portion;
wherein the first passage-forming portion and the second passage-forming portion are at least partially spaced apart at a location by a second distance,
wherein the second distance is greater than the first distance, and
wherein no portion of the gastric band crosses a tangent line that is tangent to the caudal-most point on the caudal-most curved portion.

19. A gastric band configured to be positioned on a stomach to partition the stomach into a first portion and a second portion, and to provide a passage between the first and second portions of the stomach, the gastric band comprising:
a partitioning section at least a portion of which is inflatable, the partitioning section, comprising a first end of the gastric band having a first arm with a bent end and a first elongate member extending a majority of a length of the gastric band and a second arm with a bent end and a second elongate member extending a majority of the length of the gastric band and spaced apart a first distance from the first elongate member; and
a passage-forming section comprising a second end of the gastric band, and having a curved member joining together the bent ends of the first and second arm of the partitioning section and spacing the bent ends apart by a second distance greater than the first distance.

* * * * *